(12) United States Patent
Liu et al.

(10) Patent No.: US 6,534,695 B2
(45) Date of Patent: Mar. 18, 2003

(54) IDENTIFICATION AND CHARACTERIZATION OF A DWARF AND LATE FLOWERING 2 PHENOTYPE (DLF2) IN ARABIDOPSIS

(75) Inventors: Alex Liu, Eugene, OR (US); Jill Van Winkle, Portland, OR (US); Susan Bovee-Picciano, Lafayette, OR (US); Helena Mathews, Portland, OR (US)

(73) Assignee: Agrinomics LLC, Portland, OR (US)

( * ) Notice: Subject to any disclaimer, the term of this patent is extended or adjusted under 35 U.S.C. 154(b) by 0 days.

(21) Appl. No.: 09/948,138

(22) Filed: Sep. 5, 2001

(65) Prior Publication Data

US 2002/0088028 A1 Jul. 4, 2002

Related U.S. Application Data

(60) Provisional application No. 60/230,340, filed on Sep. 6, 2000.

(51) Int. Cl.$^7$ .......................... A01H 11/00; A01H 1/00; C07H 21/02; C07H 21/04; C12N 5/04; C12N 15/82
(52) U.S. Cl. .................... 800/290; 800/295; 800/278; 536/23.1; 536/23.6; 435/468; 435/419
(58) Field of Search .................... 800/290, 295, 800/298, 278; 536/23.1, 23.6; 435/419, 468, 410

(56) References Cited

PUBLICATIONS

Finnegan et al, "Transgene Inactivation: Plants Fight Back", Sep. 1994, Bio/technology vol. 12, pp. 883–887.*
Eshed et al, Establishment of polarity in lateral organs of plants, 2001, Current Biology Vo. 11, No. 16, pp. 1251–1260.*
Bowie et al, "Decipheruing the message in protein sequences: Tolerance to amino acid substitutions", 1990, Science vol. 247, pp. 1306–1310.*
McConnell et al, Role of Phabulosa and Phavoluta in determing radial pattering in shoots, 2001, Nature vol. 411, pp. 709–713.*
Salinas et al, 1998, NCBI accession No. AF062925.*
Chao, Q. et al., "Arabidopsis T12C24, 14 Protein", Database Swall Online, Oct. 1, 2000, retrieved from EBI, database accession No. Q9NL86, XP00220641 abstract.
Lin, X. et al., "Arabidopsis F16M19.20 Protein", Database Swall Onlinel, May 1, 2000, retrieved from EBI, database accession No. Q9SGJ6, XP002200642 abstract.
Bevan, M. et al., "Arabidopsis M7J2.150 Protein", Aug. 1, 1998, retrieved from EBI, database accession No. Q65612, XP002200643 abstract.

\* cited by examiner

*Primary Examiner*—Elizabeth F. McElwain
*Assistant Examiner*—Stuart Baum
(74) *Attorney, Agent, or Firm*—Jan P. Brunelle

(57) ABSTRACT

The present invention is directed to a novel plant phenotype, designated DWARF AND LATE FLOWERING 2 (DLF2), a nucleic acid sequence expressed in plants demonstrating the DLF2 phenotype and the corresponding amino acid sequence. Also provided are plant cells and plants that exhibit modified DLF2 expression.

6 Claims, No Drawings

IDENTIFICATION AND CHARACTERIZATION OF A DWARF AND LATE FLOWERING 2 PHENOTYPE (DLF2) IN ARABIDOPSIS

REFERENCE TO RELATED APPLICATIONS

This application claims priority to provisional application No. 60/230,340 filed Sep. 6, 2000, entitled "Identification and characterization of a dwarf and late flowering phenotype in arabidopsis.

FIELD OF THE INVENTION

The present invention relates to a plant phenotype, designated DWARF AND LATE FLOWERING 2 (DLF2), together with DNA and polypeptide sequences associated with the same.

BACKGROUND OF THE INVENTION

The traditional methods for gene discovery, including chemical mutagenesis, irradiation and T-DNA insertion, used to screen loss of function mutants have limitations. Mutagenic methods such as these rarely identify genes that are redundant in the genome, and gene characterization is time-consuming and laborious.

Activation tagging is a method by which genes are randomly and strongly up-regulated on a genome-wide scale, after which specific phenotypes are screened for and selected. Isolation of mutants by activation tagging has been reported (Hayashi et al., 1992). An activation T-DNA tagging construct was used to activate genes in tobacco cell culture allowing the cells to grow in the absence of plant growth hormones (Walden et al., 1994). Genes have been isolated from plant genomic sequences flanking the T-DNA tag and putatively assigned to plant growth hormone responses. (See, e.g., Miklashevichs et al. 1997, Harling et al., 1997; Walden et. al., 1994; and Schell et al., 1998, which discusses related studies.)

The first gene characterized in Arabidopsis using activation tagging was a gene encoding the histone kinase involved in the cytokinin signal transduction pathway. The gene sequence was isolated from plant genomic DNA by plasmid rescue and the role of the gene, CKI1, in cytokinin responses in plants was confirmed by re-introduction into Arabidopsis (Kakimoto, 1996). This was followed by reports of several dominant mutants such as TINY, LHY and SHI using a similar approach along with the Ds transposable element (Wilson et al., 1996, Schaffer et al., 1998, Fridborg et al., 1999). In a more recent report, activation T-DNA tagging and screening plants for an early flowering phenotype led to the isolation of the FT gene (Kardailsky et al., 1999).

The potential application of activation tagging as a high through put technology for gene discovery has been demonstrated based on screening of several dominant mutant genes involved in photoreceptor, brassinosteroid, gibberellin and flowering signal pathways, as well as disease resistance. (See, e.g., Weigel et al., 2000, Christensen et al., 1998; Kardailsky et al., 1999).

SUMMARY OF THE INVENTION

The invention provides nucleic acid and amino acid sequences associated with the DWARF AND LATE FLOWERING 2 ("DLF2") phenotype in plants, identified for its late flowering, compact stature, and increased chlorophyll relative to wild-type Arabidopsis plants.

In one aspect, the invention provides one or more isolated DLF2 nucleic acid sequences comprising a nucleic acid sequence that encodes or is complementary to a sequence that encodes a DLF2 polypeptide having at least 70%, 80%, 90% or more sequence identity to the amino acid sequence presented as SEQ ID NO:2.

In another aspect, the polynucleotide comprises a nucleic acid sequence that hybridizes, under high, medium, or low stringency conditions to the nucleic acid sequence, or fragment thereof, presented as SEQ ID NO: 1, or the complement thereof.

In a related aspect, expression of one or more of such DLF2 polynucleotides in a plant is associated with the DLF2 phenotype.

The invention further provides plant transformation vectors, plant cells, plant parts and plants comprising a DLF2 nucleic acid sequence.

Expression of such a DLF2 nucleic acid sequence in a plant is associated with the DLF2 phenotype, presented as a late flowering, compact stature, and increased chlorophyll.

The expression of a DLF2 nucleic acid sequence may be modified in ornamental plants, fruit and vegetable-producing plants, grain-producing plants, oil-producing plants and nut-producing plants, as well as other crop plants, resulting in the DLF2 phenotype.

In a further aspect the invention provides a method of modifying the DLF2 phenotype in a plant by introducing a DLF2 nucleic acid sequence into plant progenitor cells and growing the cells to produce a transgenic plant.

DETAILED DESCRIPTION OF THE INVENTION

I. Definitions

Unless otherwise indicated, all technical and scientific terms used herein have the same meaning as they would to one skilled in the art of the present invention. Practitioners are particularly directed to Sambrook et al., 1989, and Ausubel FM et al., 1993, for definitions and terms of the art. It is to be understood that this invention is not limited to the particular methodology, protocols, and reagents described, as these may vary.

All publications cited herein, and listed below immediately after the examples, are expressly incorporated herein by reference for the purpose of describing and disclosing compositions and methodologies that might be used in connection with the invention.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence which is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403–410; blast.wustl.edu/blast/README.html website) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

The term "% homology" is used interchangeably herein with the term "% identity."

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5–10° below the Tm; "intermediate stringency" at about 10–20° below the Tm of the probe; and "low stringency" at about 20–25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a plant cell means the plant cell has a non-native (heterologous) nucleic acid sequence integrated into its genome which is maintained through two or more generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, progagules and embryos.

As used herein, the terms "native" and "wild-type" relative to a given plant trait or phenotype refers to the form in which that trait or phenotype is found in the same variety of plant in nature.

As used herein, the trem "modified" regarding a plant trait, refers to a change in the phenotype of a transgenic plant relative to a non-transgenic plant, as it is found in nature.

As used herein, the trem "$T_1$" refers to the generation of plants from the seed of $T_0$ plants. The $T_1$ generation is the first set of transformed plants that can be selected by application of a selection agent, e.g., an antibiotic or herbicide, for which the transgenic plant contains the corresponding resistance gene.

As used herein, the term "$T_2$" refers to the generation of plants by self-fertilization of the flowers of $T_1$ plants, previously selected as being transgenic.

As used herein, the trem "plant part" includes any plant organ or tissue including, without limitation, seeds, embryos, meristematic regions, callus tissue, leaves, roots, shoots, gametophytes, pollen, and micrespores. Plant cells can be obtained from any plant organ or tissue and cultures prepared therefrom. The class of plants which can be used in the methods of the present invention is generally as broad as the class of higher plants amenable to transformation techniques, icluding both monocotyledenous and dicotyledenous plants.

As used herein, "transgenic plant" includes reference to a plant that comprises within its genome a heterologous polynucleotide. Generally, the heterologous polynucleotide is stably integrated within the genome such that the polynucleotide is passed on to successive generations. The heterologous polynuclertide may be integrated unto the genome alone or as part of a recombinant expression cassette, "Transgenic" is used herein to include any cell, cell line, callus, tissue, plant part or plant, the genotype of which has been altered by the presence of heterologous nucleic acid including those transgenics initially so altered as well as those created by sexual crosses of asexual propagation from the initial transgenic.

Thus a plant having within its cells a heterologous polynucleotide is referred to jereom as a "transgenic plant". The heterologous polynucleotide can be either stably integrated into the genome, or can be extra-chromosomal. Preferably, the polynucleotide of the present invention is stably integrated into the genome suce that the polnycleotide is passed on to successive generations. The polynucleotide is integrated into the genome alone or as part of a recombinant expression cassette. "Transgenic" is used herein to include any cell, cell line, callus, tissue, plant part or plant, the genotype of which has been altered by the presence of heterologous nucleic acids including those transgenics initially so altered as well as those created by sexual crosses or asexual reproduction of the initial transgenics.

A plant cell, tissue, organ, or plant into which the recombinant DNA constructs containing the expression constructs have been introduced is considered "transformed", "transfected", or "transgenic". A transgenic or transformed cell or plant also includes progeny of the cell or plant and progeny produced from a breeding program employing such a transgenic plant as a parent in a cross and exhibiting an altered phenotype resulting from the presence of a recombinant nucleic acid sequence. Hence, a plant of the invention will. include any plant which has a cell containing a construct with introduced nucleic acid sequences, regardless of whether the sequence was introduced into the directly through transformation means or introduced by generational transfer from a progenitor cell which originally received the construct by direct transformation.

The terms "DWARF AND LATE FLOWERING 2" and "DLF2", as used herein encompass native DWARF AND LATE FLOWERING 2 (DLF2) nucleic acid and amino acid sequences, homologues, variants and fragments thereof.

An "isolated" DLF2 nucleic acid molecule is a DLF2 nucleic acid molecule that is identified and separated from at least one contaminant nucleic acid molecule with which it is ordinarily associated in the natural source of the DLF2 nucleic acid. An isolated DLF2 nucleic acid molecule is other than in the form or setting in which it is found in nature. However, an isolated DLF2 nucleic acid molecule includes DLF2 nucleic acid molecules contained in cells that ordinarily express DLF2 where, for example, the nucleic acid molecule is in a chromosomal location different from that of natural cells.

As used herein, the term "mutant" with reference to a polynucleotide sequence or gene differs from the corresponding wild type polynucleotide sequence or gene either in terms of sequence or expression, where the difference contributes to a modified plant phenotype or trait. Relative to a plant or plant line, the term "mutant"refers to a plant or plant line which has a modified plant phenotype or trait, where the modified phenotype or trait is associated with the modified expression of a wild type polynucleotide sequence or gene.

Generally, a "variant" polynucleotide sequence encodes a "variant" amino acid sequence which is altered by one or more amino acids from the reference polypeptide sequence. The variant polynucleotide sequence may encode a variant amino acid sequence having "conservative" or "non-conservative" substitutions. Variant polynucleotides may also encode variant amino acid sequences having amino acid insertions or deletions, or both.

As used herein, the term "phenotype" may be used interchangeably with the term "trait". The terms refer to a plant characteristic which is readily observable or measurable and results from the interaction of the genetic make-up of the plant with the environment in which it develops. Such a phenotype includes chemical changes in the plant make-up resulting from enhanced gene expression which may or may not result in morphological changes in the plant, but which are measurable using analytical techniques known to those of skill in the art.

As used herein, the term "interesting phenotype" with reference to a plant produced by the methods described herein refers to a readily observable or measurable phenotype demonstrated by a $T_1$ and/or subsequent generation plant, which is not displayed by a plant that has not been so transformed (and/or is not the progeny of a plant that has been so transformed) and represents an improvement in the plant. An "improvement" is a feature that may enhance the utility of a plant species or variety by providing the plant with a unique quality. By unique quality is meant a novel feature or a change to an existing feature of the plant species which is a quantitative change (increase or decrease) or a qualitative change in a given feature or trait.

II. The Identified DLF2 Phenotype and Gene

The gene and phenotype of this invention were identified in a large-scale screen using activation tagging. Activation tagging is a process by which a heterologous nucleic acid construct comprising a nucleic acid control sequence, e.g. an enhancer, is inserted into a plant genome. The enhancer sequences act to enhance transcription of a one or more native plant genes (See, e.g., Walden R, et al., 1994; Weigel D et al. 2000). Briefly, a large number of Arabidopsis plants were transformed with the activation tagging vector pSKI015 (Weigel et al, 2000), which comprises a T-DNA (i.e., the sequence derived from the Ti plasmid of Agrobacterium tumifaciens that are transferred to a plant cell host during Agrobacteriuni infection), an enhancer element and a selectable marker gene. Following random insertion of pSK1015 into the genome of transformed plants, the enhancer element can result in up-regulation genes in the vicinity of the T-DNA insertion, generally within 5–10 kilobase (kb) of the insertion. In the $T_1$ generation, plants were exposed to the selective agent in order to specifically recover those plants that expressed the selectable marker and therefore harbored insertions of the activation-tagging vector. Transformed plants were observed for interesting phenotypes, which are generally identified at the $T_1$, $T_2$ and/or $T_3$ generations. Interesting phenotypes may be identified based on morphology, a biochemical screen, herbicide tolerance testing, herbicide target identification, fungal or bacterial resistance testing, insect or nematode resistance testing, screening for stress tolerance, such as drought, salt or antibiotic tolerance, and output traits, such as oil, starch, pigment, or vitamin composition. Genomic sequence surrounding the T-DNA insertion is analyzed in order to identify genes responsible for the interesting phenotypes. Genes responsible for causing such phenotypes are identified as attractive targets for manipulation for agriculture, food, ornamental plant, and/or pharmaceutical industries.

It will be appreciated that in most cases when a modified phenotype results from the enhanced expression of a tagged gene, the phenotype is dominant. In some cases, the enhanced expression of a given native plant gene or a fragment thereof may result in decreased expression or inactivation of its homologue or another native plant gene, which results in the interesting phenotype. The T-DNA insertion may also result in disruption ("loss-of-function") of a native plant gene, in which case the phenotype is generally recessive.

The present invention provides a late flowering, compact stature, and increased chlorophyll phenotype, identified in T₁, T₂, and T₃ plants of an ACTTAG Arabidopsis line. The phenotype and associated gene have been designated DWARF AND LATE FLOWERING 2 ("DLF2").

The invention also provides a newly identified and isolated nucleic acid sequence that was identified by analysis of the genomic DNA sequence surrounding the T-DNA insertion correlating with the DLF2 phenotype. In particular, applicants have identified and characterized the open reading frame of the DLF2 gene, which is specifically overexpressed in plants having the DLF2 phenotype, and which is provided in SEQ ID NO:1. A detailed description of the isolation and characterization of DLF2 is set forth in the Examples.

III. Compositions of the Invention
A. DLF2 Nucleic Acids

The DLF2 gene may be used in the development of transgenic plants having a desired phenotype. This may be accomplished using the native DLF2 sequence, a variant DLF2 sequence or a homologue or fragment thereof.

A DLF2 nucleic acid sequence of this invention may be a DNA or RNA sequence, derived from genomic DNA, cDNA or mRNA. The nucleic acid sequence may be cloned, for example, by isolating genomic DNA from an appropriate source, and amplifying and cloning the sequence of interest using PCR. Alternatively, nucleic acid sequence may be synthesized, either completely or in part, especially where it is desirable to provide plant-preferred sequences. Thus, all or a portion of the desired structural gene (that portion of the gene which encodes a polypeptide or protein) may be synthesized using codons preferred by a selected host.

The invention provides a polynucleotide comprising a nucleic acid sequence which encodes or is complementary to a sequence which encodes a DLF2 polypeptide having the amino acid sequence presented in SEQ ID NO:2 and a polynucleotide sequence identical over its entire length to the DLF2 nucleic acid sequence presented SEQ ID NO:1. The invention also provides the coding sequence for the mature DLF2 polypeptide, a variant or fragment thereof, as well as the coding sequence for the mature polypeptide or a fragment thereof in a reading frame with other coding sequences, such as those encoding a leader or secretory sequence, a pre-, pro-, or prepro- protein sequence.

A DLF2 polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include poiynucleotides comprising a structural gene and the naturally associated sequences that control gene expression.

When an isolated polynucleotide of the invention comprises a DLF2 nucleic acid sequence flanked by non-DLF2 nucleic acid sequence, the total length of the combined polynucleotide is typically less than 25 kb, and usually less than 20 kb, or 15 kb, and in some cases less than 10 kb, or 5 kb.

In addition to the DLF2 nucleic acid and corresponding polypeptide sequences described herein, it is contemplated that DLF2 variants can be prepared. DLF2 variants can be prepared by introducing appropriate nucleotide changes into the DLF2 nucleic acid sequence; by synthesis of the desired DLF2 polypeptide or by altering the expression level of the DLF2 gene in plants. Those skilled in the art will appreciate that amino acid changes may alter post-translational processing of the DLF2 polypeptide, such as changing the number or position of glycosylation sites or altering the membrane anchoring characteristics.

In one aspect, preferred DLF2 coding sequences include a polynucleotide comprising a nucleic acid sequence which encodes or is complementary to a sequence which encodes a DLF2 polypeptide having at least 50%, 60%, 70%, 75%, 80%, 85%, 90%, 95% or more sequence identity to the amino acid sequence presented in SEQ ID NO:2.

In another aspect, preferred variants include a DLF2 polynucleotide sequence that is at least 50% to 60% identical over its entire length to the DLF2 nucleic acid-sequence presented as SEQ ID NO:1, and nucleic acid sequences that are complementary to such a DLF2 sequence. More preferable are DLF2 polynucleotide sequences comprise a region having at least 70%, 80%, 85%, 90% or 95% or more sequence identity to the DLF2 sequence presented as SEQ ID NO:1.

In a related aspect, preferred variants include polynucleotides that are be "selectively hybridizable" to the DLF2 polynucleotide sequence presented as SEQ ID NO:1.

Sequence variants also include nucleic acid molecules that encode the same polypeptide as encoded by the DLF2 polynucleotide sequencedescribed herein. Thus, where the coding frame of an identified nucleic acid molecules is known, for example by homology to known genes or by extension of the sequence, it is appreciated that as a result of the degeneracy of the genetic code, a number of coding sequences can be produced. For example, the triplet CGT encodes the amino acid arginine. Arginine is alternatively encoded by CGA, CGC, CGG, AGA, and AGG. Therefore it is appreciated that such substitutions in the coding region fall within the sequence variants that are covered by the present invention. Any and all of these sequence variants can be utilized in the same way as described herein for the identified DLF2 parent sequence, SEQ ID NO:1.

It is further appreciated that such sequence variants may or may not selectively hybridize to the parent sequence. This would be possible, for example, when the sequence variant includes a different codon for each of the amino acids encoded by the parent nucleotide. Such variants are, nonetheless, specifically contemplated and encompassed by the present invention. In accordance with the present invention, also encompassed are sequences that at least 70% identical to such degeneracy-derived sequence variants.

Although DLF2 nucleotide sequence variants are preferably capable of hybridizing to the nucleotide sequences recited herein under conditions of moderately high or high stringency, there are, in some situations, advantages to using variants based on the degeneracy of the code, as described above. For example, codons may be selected to increase the rate at which expression of the peptide occurs in a particular prokaryotic or eukaryotic organism, in accordance with the optimum codon usage dictated by the particular host organism. Alternatively, it may be desirable to produce RNA having longer half lives than the mRNA produced by the recited sequences.

Variations in the native full-length DLF2 nucleic acid sequence described herein, may be made, for example, using any of the techniques and guidelines for conservative and non-conservative mutations, as generally known in the art, oligonucleotide-mediated (site-directed) mutagenesis, alanine scanning, and PCR mutagenesis. Site-directed mutagenesis (Kunkel TA et al., 1991); cassette mutagenesis (Crameri A et al., 1995); restriction selection mutagenesis (Haught C et al., 1994), or other known techniques can be performed on the cloned DNA to produce nucleic acid sequences encoding DLF2 variants.

It is contemplated that the gene sequences associated with the DLF2 phenotype may be synthesized, either completely or in part, especially where it is desirable to provide host-preferred sequences. Thus, all or a portion of the desired structural gene (that portion of the gene which encodes the protein) may be synthesized using codons preferred by a selected host. Host-preferred codons may be determined, for example, from the codons used most frequently in the proteins expressed in a desired host species.

It is preferred that a DLF2 polynucleotide encodes a DLF2 polypeptide that retains substantially the same biological function or activity as the mature DLF2 polypeptide encoded by the polynucleotide set forth as SEQ ID NO:1 (i.e. results in a DLF2 phenotype when overexpressed in a plant).

Variants also include fragments of the DLF2 polynucleotide of the invention, which can be used to synthesize a full-length DLF2 polynucleotide. Preferred embodiments include polynucleotides encoding polypeptide variants wherein 5 to 10, 1 to 5, 1 to 3, 2, 1 or no amino acid residues of a DLF2 polypeptide sequence of the invention are substituted, added or deleted, in any combination. Particularly preferred are substitutions, additions, and deletions that are silent such that they do not alter the properties or activities of the polynucleotide or polypeptide.

A nucleotide sequence encoding a DLF2 polypeptide can also be used to construct hybridization probes for further genetic analysis. Screening of a cDNA or genomic library with the selected probe may be conducted using standard procedures, such as described in Sambrook et al., 1989). Hybridization conditions, including moderate stringency and high stringency, are provided in Sambrook et al., supra.

The probes or portions thereof may also be employed in PCR techniques to generate a pool of sequences for identification of closely related DLF2 sequences. When DLF2 sequences are intended for use as probes, a particular portion of a DLF2 encoding sequence, for example a highly conserved portion of the coding sequence may be used.

For example, a DLF2 nucleotide sequence may be used as a hybridization probe for a cDNA library to isolate genes, for example, those encoding naturally-occurring variants of DLF2 from other plant species, which have a desired level of sequence identity to the DLF2 nucleotide sequence disclosed in SEQ ID NO:1. Exemplary probes have a length of about 20 to about 50 bases.

In another exemplary approach, a nucleic acid encoding a DLF2 polypeptide may be obtained by screening selected cDNA or genomic libraries using the deduced amino acid sequence disclosed herein, and, if necessary, using conventional primer extension procedures as described in Sambrook et al., supra, to detect DLF2 precursors and processing intermediates of mRNA that may not have been reverse-transcribed into cDNA.

As discussed above, nucleic acid sequences of this invention may include genomic, cDNA or mRNA sequence. By "encoding" is meant that the sequence corresponds to a particular amino acid sequence either in a sense or anti-sense orientation. By "extrachromosomal" is meant that the sequence is outside of the plant genome of which it is naturally associated. By "recombinant" is meant that the sequence contains a genetically engineered modification through manipulation via mutagenesis, restriction enzymes, and the like.

Once the desired formn of a DLF2 nucleic acid sequence, homologue, variant or fragment thereof, is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

With or without such modification, the desired form of the DLF2 nucleic acid sequence, homologue, variant or fragment thereof, may be incorporated into a plant expression vector for transformation of plant cells.

B. DLF2 Polypeptides

In one preferred embodiment, the invention provides a DLF2 polypeptide, having a native mature or full-length DLF2 polypeptide sequence comprising the sequence presented in SEQ ID NO:2. A DLF2 polypeptide of the invention can be the mature DLF2 polypeptide, part of a fusion protein or a fragment or variant of the DLF2 polypeptide sequence presented in SEQ ID NO:2.

Ordinarily, a DLF2 polypeptide of the invention has at least 50% to 60% identity to a DLF2 amino acid sequence over its entire length. More preferable are DLF2 polypeptide sequences that comprise a region having at least 70%, 80%, 85%, 90% or 95% or more sequence identity to the DLF2 polypeptide sequence of SEQ ID NO:2.

Fragments and variants of the DLF2 polypeptide sequence of SEQ ID NO:2, are also considered to be a part of the invention. A fragment is a variant polypeptide that has an amino acid sequence that is entirely the same as part but not all of the amino acid sequence of the previously described polypeptides. Exemplary fragments comprises at least 10, 20, 30, 40, 50, 75, or 100 contiguous amino acids of SEQ ID NO:2. The fragments can be "free-standing" or comprised within a larger polypeptide of which the fragment forms a part or a region, most preferably as a single continuous region. Preferred fragments are biologically active fragments, which are those fragments that mediate activities of the polypeptides of the invention, including those with similar activity or improved activity or with a decreased activity. Also included are those fragments that antigenic or immunogenic in an animal, particularly a human:

DLF2 polypeptides of the invention also include polypeptides that vary from the DLF2 polypeptide sequence of SEQ ID NO:2. These variants may be substitutional, insertional or deletional variants. The variants typically exhibit the same qualitative biological activity as the naturally occurring analogue, although variants can also be selected which have modified characteristics as further described below.

A "substitution" results from the replacement of one or more nucleotides or amino acids by different nucleotides or amino acids, respectively.

An "insertion" or "addition" is that change in a nucleotide or amino acid sequence which has resulted in the addition of one or more nucleotides or amino acid residues, respectively, as compared to the naturally occurring sequence.

A "deletion" is defined as a change in either nucleotide or amino acid sequence in which one or more nucleotides or amino acid residues, respectively, are absent.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances.

Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids.

Substitutions are generally made in accordance with known "conservative substitutions". A "conservative substitution" refers to the substitution of an amino acid in one class by an amino acid in the same class, where a class is defined by common physicochemical amino acid side chain properties and high substitution frequencies in homologous proteins found in nature (as determined, e.g., by a standard Dayhoff frequency exchange matrix or BLOSUM matrix). (See generally, Doolittle, R. F., 1986.)

A "non-conservative substitution" refers to the substitution of an amino acid in one class with an amino acid from another class.

DLF2 polypeptide variants typically exhibit the same qualitative biological activity as the naturally occurring analogue, although variants also are selected to modify the characteristics of the DLF2 polypeptide, as needed. For example, glycosylation sites, and more particularly one or more O-linked or N-linked glycosylation sites may be altered or removed. Those skilled in the art will appreciate that amino acid changes may alter post-translational processes of the DLF2 polypeptide, such as changing the number or position of glycosylation sites or altering the membrane anchoring characteristics.

The variations can be made using methods known in the art such as oligonucleotide-mediated (site-directed) mutagenesis, alanine scanning, and PCR mutagenesis. Site-directed mutagenesis [Carter et al., 1986; Zoller et al., 1987], cassette mutagenesis [Wells et al., 1985], restriction selection mutagenesis [Wells et al., 1986] or other known techniques can be performed on the cloned DNA to produce the DLF2 polypeptide-encoding variant DNA.

Also included within the definition of DLF2 polypeptides are other related DLF2 polypeptides. Thus, probe or degenerate PCR primer sequences. may be used to find other related polypeptides. Useful probe or primer sequences may be designed to all or part of the DLF2 polypeptide sequence, or to sequences outside the coding region. As is generally known in the art, preferred PCR primers are from about 15 to about 35 nucleotides in length, with from about 20 to about 30 being preferred, and may contain inosine as needed. The conditions for the PCR reaction are generally known in the art.

Covalent modifications of DLF2 polypeptides are also included within the scope of this invention. For example, the invention provides DLF2 polypeptides that are a mature protein and may comprise additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes can be used to remove any additional amino acids from the mature protein. [See, e.g., Creighton, TE, 1983].

In a preferred embodiment, overexpression of a DLF2 polypeptide or variant thereof is associated with the DLF2 phenotype.

C. Antibodies.

The present invention further provides anti-DLF2 polypeptide antibodies. The antibodies may be polyclonal, monoclonal, humanized, bispecific or heteroconjugate antibodies.

Methods of preparing polyclonal antibodies are known to the skilled artisan. Such polyclonal antibodies can be produced in a mammal, for example, following one or more injections of an immunizing agent, and preferably, an adjuvant. Typically, the immunizing agent and/or adjuvant will be injected into the mammal by a series of subcutaneous or intraperitoneal injections. The immunizing agent may include a DLF2 polypeptide or a fusion protein thereof. It may be useful to conjugate the antigen to a protein known to be immunogenic in the mammal being immunized. The immunization protocol may be determined by one skilled in the art based on standard protocols or by routine experimentation.

Alternatively, the anti-DLF2 polypeptide antibodies may be monoclonal antibodies. Monoclonal antibodies may be produced by hybridomas, wherein a mouse, hamster, or other appropriate host animal, is immunized with an immunizing agent to elicit lymphocytes that produce or are capable of producing antibodies that will specifically bind to the immunizing agent [Kohler et al., 1975]. Monoclonal antibodies may also be made by recombinant DNA methods, such as those described in U.S. Pat. No. 4,816,567.

The anti-DLF2 polypeptide antibodies of the invention may further comprise humanized antibodies or human antibodies. The term "humanized antibody" refers to humanized forms of non-human (e.g., murine) antibodies that are chimeric antibodies, immunoglobulin chains or fragments thereof (such as Fv, Fab, Fab', $F(ab')_2$ or other antigen-binding partial sequences of antibodies) which contain some portion of the sequence derived from non-human antibody. Methods for humanizing non-human antibodies are well known in the art, as further detailed in Jones et al., 1986; Riechmann et al., 1988; and Verhoeyen et al., 1988. Methods for producing human antibodies are also known in the art. See, e.g., Jakobovits, A, et al., 1995; Jakobovits, A, 1995.

In one exemplary approach, anti-DLF2 polyclonal antibodies are used for gene isolation. Western blot analysis may be conducted to determine that DLF2 or a related protein is present in a crude extract of a particular plant species. When reactivity is observed, genes encoding the related protein may be isolated by screening expression libraries representing the particular plant species. Expression libraries can be constructed in a variety of commercially available vectors, including lambda gt11, as described in Sambrook, et al. , 1989.

IV. Utility Of the DLF2 Phenotype and Gene

From the foregoing, it can be appreciated that the DLF2 nucleotide sequence, protein sequence and phenotype find utility in modulated expression of the DLF2 protein and the development of non-native phenotypes associated with such modulated expression.

The DLF2 late flowering, compact stature, and increased chlorophyll traits distinguish the mutant from wild type Arabidopsis. The mutant has short stature and late blooming characteristics compared to wild plants without any reduction in the total number or size of flowers or siliques.

There are several possible applications of this feature. The compact stature feature is an attractive trait to be incorporated to turf grass in reducing the mowing frequency of the lawns. Shortening of plant height will be a boon for application in fruit trees such as banana, mango, litchee, jackfruit and palm trees such as date palm, coconut palm which are several meters high. Modification in plant height in the latter group of plants would lead to manageable procedures in fruit harvest and there by, increased fruit production due to wastage/harvesting problems. There is potential for higher planting density per unit area, as the short height would allow more tiers of planting especially in hydroponic systems.

Higher yield per unit resources (such as water and fertilizer) is another advantage when the plant height is reduced since the total consumption of water and nutrients will be lesser for plants of small stature compared to tall plants. The dwarf trait will be much appreciated by nurseries involved in bonsai plants and other cut flower industries. The dwarf trait would be ideal to those cereals where lodging is a serious problem with increased grain production.

The late flowering trait can be suitably modulated to fit certain seasonal/short day/long day plants such that year-round flowering and fruiting can be accomplished especially in ornamental or fruit plants. The observed morphology is one version of the phenotype: The gene could be modulated with regard to the level of expression, the tissue types, and the tissue specificity of expression, which may provide a wide spectrum of applications for the discovered traits. For example, the dwarf phenotype may be expressed in certain areas, organs, or tissues. Similarly the late flowering trait may be temporally regulated such that flowering is induced at certain intervals in a plant instead of one flush of flowering throughout the plant or during only one season.

In practicing the invention, the DLF2 phenotype and modified DLF2 expression is generally applicable to any type of plant.

The methods described herein are generally applicable to all plants. Although activation tagging and gene identification is carried out in Arabidopsis, following identification of a nucleic acid sequence and associated phenotype, the selected gene, a homologue, variant or fragment thereof, may be expressed in any type of plant. In one aspect, the invention is directed to fruit- and vegetable-bearing plants. In a related aspect, the invention is directed to the cut flower industry, grain-producing plants, oil-producing plants and nut-producing plants, as well as other crops including, but not limited to, cotton (Gossypium), alfalfa (Medicago sativa), flax (Linum usitatissimum), tobacco (Nicotiana), turfgrass (Poaceae family), and other forage crops.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to Agrobacterium-mediated transformation, electroporation, microinjection, microprojectile bombardment calcium-phosphate-DNA co-precipitation or liposome-mediated transformation of a heterologous nucleic acid construct comprising the DLF2 coding sequence. The transformation of the plant is preferably permanent, i.e. by integration of the introduced expression constructs into the host plant genome, so that the introduced constructs are passed onto successive plant generations.

In one embodiment, binary Ti-based vector systems may be used to transfer and confirm the association between enhanced expression of an identified gene with a particular plant trait or phenotype. Standard Agrobacterium binary vectors are known to those of skill in the art and many are commercially available, such as pBI121 (Clontech Laboratories, Palo Alto, Calif.).

The optimal procedure for transformation of plants with Agrobacterium vectors will vary with the type of plant being transformed. Exemplary methods for Agrobacterium-mediated transformation include transformation of explants of hypocotyl, shoot tip, stem or leaf tissue, derived from sterile seedlings and/or plantlets. Such transformed plants may be reproduced sexually, or by cell or tissue culture. Agrobacterium transformation has been previously described for a large number of different types of plants and methods for such transformation may be found in the scientific literature.

Depending upon the intended use, a heterologous nucleic acid construct may be made which comprises a nucleic acid sequence associated with the DLF2 phenotype, and which encodes the entire protein, or a biologically active portion thereof for transformation of plant cells and generation of transgenic plants.

The expression of a DLF2 nucleic acid sequence or a homologue, variant or fragment thereof may be carried out under the control of a constitutive, inducible or regulatable promoter. In some cases expression of the DLF2 nucleic acid sequence or homologue, variant or fragment thereof may regulated in a developmental stage or tissue-associated or tissue-specific manner. Accordingly, expression of the nucleic acid coding sequences described herein may be regulated with respect to the level of expression, the tissue type(s) where expression takes place and/or developmental stage of expression leading to a wide spectrum of applications wherein the expression of a DLF2 coding sequence is modulated in a plant.

Strong promoters with enhancers may result in a high level of expression. When a low level of basal activity is desired, a weak promoter may be a better choice. Expression of DLF2 nucleic acid sequence or homologue, variant or fragment thereof may also be controlled at the level of transcription, by the use of cell type specific promoters or promoter elements in the plant expression vector.

Numerous promoters useful for heterologous gene expression are available. Exemplary constitutive promoters include the raspberry E4 promoter (U.S. Pat. Nos. 5,783,393 and 5,783,394), the 35S CaMV (Jones J D et al, 1992), the CsVMV promoter (Verdaguer B et al., 1998) and the melon actin promoter. Exemplary tissue-specific promoters include the tomato E4 and E8 promoters (U.S. Pat. No. 5,859,330) and the tomato 2AII gene promoter (Van Haaren M J J et al., 1993).

When DLF2 sequences are intended for use as probes, a particular portion of a DLF2 encoding sequence, for example a highly conserved portion of a coding sequence may be used.

In yet another aspect, in some cases it may be desirable to inhibit the expression of endogenous DLF2 sequences in a host cell. Exemplary methods for practicing this aspect of the invention include, but are not limited to antisense suppression (Smith, et al., 1988); co-suppression (Napoli, etal., 1989); ribozymes (PCT Publication WO 97/10328); and combinations of sense and antisense (Waterhouse, et al., 1998). Methods for the suppression of endogenous sequences in a host cell typically employ the transcription or transcription and translation of at least a portion of the sequence to be suppressed. Such sequences may be homologous to coding as well as non-coding regions of the endogenous sequence. In some cases, it may be desirable to inhibit expression of the DLF2 nucleotide sequence. This may be accomplished using procedures generally employed by those of skill in the art together with the DLF2 nucleotide sequence provided herein.

Standard molecular and genetic tests may be performed to analyze the association between a cloned gene and an observed phenotype. A number of other techniques that are useful for determining (predicting or confirming) the function of a gene or gene product in plants are described below.

1. DNA/RNA Analysis

DNA taken form a mutant plant may be sequenced to identify the mutation at the nucleotide level. The mutant phenotype may be rescued by overexpressing the wild type (WT) gene. The stage- and tissue-specific gene expression patterns in mutant vs. WT lines, for instance, by in situ hybridization, may be determined. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing (VIGS, see Baulcombe D, 1999).

In a preferred application, microarray analysis, also known as expression profiling or transcript profiling, is used to simultaneously measure differences or induced changes in the expression of many different genes. Techniques for microarray analysis are well known in the art (Schena M et al., Science (1995) 270:467–470; Baldwin D et al., 1999; Dangond F, Physiol Genomics (2000) 2:53–58; van Hal NL et al., J Biotechnol (2000) 78:271–280; Richmond T and Somerville S, Curr Opin Plant Biol (2000) 3:108–116). Microarray analysis of individual tagged lines may be carried out, especially those from which genes have been isolated. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical or signaling pathway based on its overexpression phenotype or by sequence homology with related genes. Alternatively, analysis may comprise genetic crosses with WT lines and other mutant lines (creating double mutants) to order the gene in a pathway, or determining the effect of a mutation on expression of downstream "reporter" genes in a pathway.

4. Other Analyses

Other analyses may be performed to determine or confirm the participation of the isolated gene and its product in a particular metabolic or signaling pathway, and to help determine gene function.

All publications, patents and patent applications are herein expressly incorporated by reference in their entirety.

While the invention has been described with reference to specific methods and embodiments, it will be appreciated that various modifications and changes may be made without departing from the invention.

EXAMPLE 1

Generation of Plants with a DLF2 Phenotype by Transformation with an Activation Tagging Construct A. Agrobacterium Vector Preparation.

Mutants were generated using the activation tagging "ACTTAG" vector, pSKI015 (GenBank Identifier [GI] 6537289; Weigel D et al., 2000).).

Transformed *E. coli* colonies and cultures containing the pSKI015 activation tagging construct was confirmed by selection on media containing 100 µg/ml ampicillin. Agrobacterium colonies and cultures were grown in selective media containing 100 µg/ml carbenicillin. The presence of the pSKI015 construct was verified in colonies by PCR primers that span the ocs terminator in the BAR selection cassette under the following PCR conditions: 30 cycles of 94° C. 30 seconds; 63° C. 40 seconds; 72° C. 120 seconds.

For long-term storage, PCR-positive colonies were grown in selective media, glycerol added to a final concentration of 30% and cultures quick frozen then stored at −80° C. For the initiation of dense Agrobacterium cultures for plant transformation, stock cultures were grown in selective media, glycerol added to a final concentration of 30%, and a number of 20 µl aliquots quick frozen in liquid nitrogen and stored at −80° C.

pSKI015 was maintained in Agrobacterium GV3101 without the helper plasmid and in Agrobacterium strain EHA 105. An Agrobacterium culture was prepared by starting a 50 ml culture 4–5 days prior to plant transformation (e.g., by "dunking"). Liquid cultures were grown at 28° C., on an orbital shaker at 200 rpm, in LBB with Carbenicillin (Cb) at 100 mg/l to select for the plasmid, with 50 mg/l Kanamycin (Kan) added to select for the helper plasmid. After 2 days, this small culture was used to inoculate 6–8 liters (L) of LBB with Cb 100 mg/l and Kan 50 mg/l, 1L each in 2000 ml Erlenmeyer flasks. Cultures are placed on a shaker for 2–3 days, checked for cell concentration by evaluating the $OD_{600}$ (visible light at 600 nm) using a spectrophotometer with an $OD_{600}$ reading for between 1.5–2.5 preferred. The cultures were then centrifuged at 4,500 RCF for 15 minutes at room temperature (18–22° C.), the bacteria resuspended to approximately $OD_{600}$=8.0 with about 500 ml per dunking vessel. Approximately 15–20 liters were prepared for 200 pots, and 20–30 plants dunked at a time.

B. Growth and Selection of Arabidopsis Thaliana Plants

Arabidopsis plants were grown in Premier HP soil which contains peat moss and perlite, using a minimal amount of N-P-K (171-2-133) fertilizer diluted to 1/10 the strength, with sub-irrigation, as needed and a n 18 hr day length using natural light supplemented by high pressure sodium lamps at a temperature of 20–25° C. Seeds were sown under humidity domes for the first 4–7 days, then transferred to a greenhouse having approximately 70% humidity.

Healthy Arabidopsis plants were grown from wild type Arabidopsis seed, Ecotype: Col-0, under long days (16 hrs) in pots in soil covered with bridal veil or window screen, until they flowered.

Plants began flowering after about 3–4 weeks, with watering and fertilizing continued as needed until a majority of the siliques turned yellow/brown. Then plants were then left to dry and seed collected by breaking open siliques to release the seed. Seed was stored at room temperature for a few days, then stored at 4° C. in an airtight container with desiccant.

Plants are monitored for pests and pathogens, particularly, fungus gnats, white flies, and aphids, with pest control applied as needed, e.g., application of Talstar and Azatin for whitefly, thrips and fungus gnats; application of Gnatrol for fungus gnats, biological control (e.g. mites, for gnat larvae) and safer soap.

Transformation was accomplished via a floral dip method wherein floral tissues were dipped into a solution containing Agrobacterium tumefaciens, 5% sucrose and a surfactant Silwet L-77, as described in Cough, S J and Bent, A F, 1998.

Briefly, above-ground parts of 2,000–3,000 plants were dipped (dunked) into an Agrobacterium culture (GV3101 with pMP90RK, helper plasmid) carrying ACTTAG (binary plasmid pSKI.015), 2–3 days after clipping for 15 minutes, with gentleagitation, then placing plants on their sides under a humidity dome or cover for 16–24 hours to maintain high humidity.

A second dunking was carried out 6 days after removing the humidity domes, as described above. Plants were watered regularly until seeds were mature, at which time watering was stopped.

C. Selection Of Transgenic Plants

Dry $T_1$ seed was harvested from transformed plants and stored at 4° C. in Eppendorf tubes with desiccant. Transformants were selected at the $T_1$ stage by sprinkling $T_1$ seed on a flat, cold treating the flats for 2 to 3 days and spraying plants as soon as they germinated with Finale (Basta, glufosinate ammonium), diluted at 1:1000 of an 11.33% solution, followed by subsequent sprayings a day or two apart.

Following sprayings, non-transgenic seedlings produced chlorotic primary leaves and their hypocotyls dehydrated and collapsed, killing the plant. The survivors were counted and segregation data calculated after the non-transgenic plants had died (within two-three weeks following the sprayings). Survivors were transplanted into individual pots for further monitoring.

Images of each pool of plants were recorded using a Digital camera (DC-260), and morphology observations were taken from plants that exhibited an interesting phenotype. These plants were grown until seed was produced, which was collected and sown to yield $T_2$ plants.

The ACTTAG™ line, W000010438 ("DLF2") was originally identified as having late flowering and compact stature in the $T_1$ plants.

Interesting $T_1$ plants were grown until they produced $T_2$ seed, which was collected and planted. The phenotype of the $T_2$ plants was described as exhibiting late flowering, compact stature, and increased chlorophyll relative to wild type Arabidopsis plants, as were the $T_3$ plants.

An increase in leaf number is closely correlated with a delay in the transition to flowering in Arabidopsis (Napp-Zinn et al., 1985). Consistent with Napp-Zinn's observation, DLF2 mutants averaged 24 rosette leaves, whereas wild-type plants averaged 13 leaves. Refer also to EXAMPLE 3 for description of the $F_1$ plants.

TABLE 1

Flowering time and plant height of DLF2 mutants.

| Genotype | Flowering Days | Number of Rosette Leaves | Plant Height |
| --- | --- | --- | --- |
| COL-0 | 27.4 ± 1.2 | 12.9 ± 1.1 | 23.7 ± 3.4 |
| F1 | 30.9 ± 1.7 | 15.8 ± 2.0 | 14.5 ± 1.4 |
| DLF2 | 41.4 ± 2.6 | 22.7 ± 2.9 | 11.1 ± 1.0 |

Recessive mutants of similar phenotype, such as ga, gai, spindly, bri, and many dwf alleles have been identified involving gibberellin or Brassinosteroid biosynthesis and signals, have been described (Michaels and Amasina, 1999; Xu et al., 1999; Peng et al., 1997; Jacobsen et al., 196; Choe et al., 1998; and Li and Chory, 1997).

EXAMPLE 2

Characterization of Plants That Exhibit the DLF2 Phenotype

A. Genomic DNA Extraction and Analysis.

Nucleon™ PhytoPure™ systems from Amersham™ were used to extract genomic DNA from $T_2$ plant tissue. Methods were essentially as follows:

1.0 g of fresh plant tissue was ground in liquid nitrogen to yield a free flowing powder, then transferred to a 15-ml polypropylene centrifuge tube. 4.6 ml of Reagent 1 from the Nucleon Phytopure kit was added with thorough mixing followed by addition of 1.5 ml of Reagent 2 from the Nucleon Phytopure kit, with inversion until a homogeneous mixture was obtained. The mixture was incubated at 65° C. in a shaking water bath for 10 minutes, and placed on ice for 20 minutes. The samples were removed from the ice, 2 ml of −20° C. chloroform added, mixed and centrifuged at 1300 g for 10 minutes. The supernatant was transferred to a fresh tube, 2 ml cold chloroform, 200 µl of Nucleon PhytoPure DNA extraction resin suspension added and the mixture shaken on a tilt shaker for 10 minutes at room temperature, then centrifuged at 1300 g for 10 minutes. Without disturbing the Nucleon resin suspension layer, the upper DNA containing phase was transferred to a fresh tube, centrifuged at 9500 rpm for 30 minutes to clarify the transferred aqueous phase, an equal volume of cold isopropanol added, the tube gently inverted until the DNA precipitated and then it was pelleted by centrifugation, washed with cold 70% ethanol, pelleted again and air-dried.

DNA extracted from plants with the DLF2 phenotype (DLF2) and from wild type plants (COL-0) was PCR amplified using primers that amplify a 35S enhancer sequence, and primers that amplify a region of the pBluescript vector sequence in pSKI015. Amplification using primers that span the 35S enhancer region resulted in a ladder of products, indicating that all four copies of the 35S enhancer were present. Amplification using primers to the pBluescript vector was done primarily to detect the T-DNA insert(s) in transformed plants and has been optimized for the following conditions: annealing temp: 57° C., 30 cycles [94° C., 30 sec; 57° C., 1 min; 72° C., 1 min] 1 cycle [72° C., 7 min].

The ACTTAG™ line, W000010438 (DLF2), was confirmed as positive for the presence of 35S enhancer and pSKI015 vector sequences by PCR, and as positive for Southern hybridization verifying genomic integration of the ACTTAG DNA and showing the presence of a tandem repeat of the T-DNA insertion in the transgenic line.

B. Plasmid Rescue

Genomic DNA from $T_2$ plants of insertion line, W000010438 ("DLF2"), was digested by restriction enzymes. The restriction fragments were self-ligated and used to transform the E. coli cells. The plasmids that contained a full-length pBluescript vector, 4×35S enhancer, and a right border T-DNA flanking genomic DNA fragment were rescued. Methods were essentially as follows:

Genomic DNA was digested with Pst I, EcoR I, BamH I, Spe I, Hind III and/or Xho I under standard reaction conditions at 37° C. overnight. Briefly, each restriction enzyme was heat inactivated at 65° C. for 20 minutes, phenol/chloroform and chloroform isoamyl (24:1) extracted once with each, and the ligation reactions were set up containing the reagents set forth below and left at 16° C. overnight.

| | |
|---|---|
| Digested Genomic DNA | 40 µl |
| 5X Ligation Buffer | 50 µl |
| Ligase (Gibcol, 1U/µl) | 10 µl |
| ddH$_2$O | 150 µl |

The ligated DNA was precipitated, resuspended in ddH2O and used to transform *E. coli* SURE cells (Stratagene) via electroporation, with 10 pg of pUC18 plasmid as a control.

The transformation mixture was spread on two LB-plates containing 100 pig/ml ampicillin and incubated overnight at 37° C. Single colonies were picked from the plates and used to start a 5 ml LB-ampicillin broth culture from each colony by culturing overnight at 37° C. The plasmid was extracted from the culture and restriction digested to confirm the size of genomic insertion.

C. Sequencing Of Rescued Plasmids

Sequencing was accomplished using a ABI Prism Big-Dye™ Terminator Cycle Sequencing Ready Reaction Kit (PE Applied Biosystem), AmpliTaq DNA Polymerase (Perkin-Elmer), an ABI Prism™ 310 Genetic Analyzer (Perkin-Elmer) and sequence analysis software, e.g., Sequencer™ 3.1.1 or MacVector 6.5.3.

An ABI Prism BigDye™ Terminator-Cycle Sequencing Ready Reaction Kit was used to sequence a rescued plasmid using an ABI Prism™ 310 Genetic Analyzer following the protocols from the manufacturer.

The left ends of plasmids rescued were sequenced across the right T-DNA border. The rescued sequence was subjected to a basic BLASTN search using the sequence comparison program available at the www.ncbi.nlm.nih.gov/BLAST website and a search of the Arabidopsis Information Resource (TAIR) database, available at the Arabidopsis.org website, which revealed sequence identity to BAC clone T12C24. This BAC is mapped to chromosome 1.

Using GENSCAN, several predicted genes were found in the in the vicinity of the T-DNA insertion, (i.e., within ~5–10 kb) and were subjected to further characterization by RT-PCR. The RT-PCR results showed that the gene whose nucleotide sequence is presented as SEQ ID NO: 1 (DLF2) was overexpressed in tissue from plants having the DLF2 phenotype.

Specifically, RNA was extracted from tissues derived from plants exhibiting the DLF2 phenotype and from wild type COL-0 plants. RT-PCR was performed using primers specific to the sequence presented as SEQ ID NO:1, which was identified following plasmid rescue, and a constitutively expressed kinase (positive control). The results showed that plants displaying the DLF2 phenotype over-expressed the mRNA for the DLF2 gene, indicating the enhanced expression of the DLF2 gene is correlated with the DLF2 phenotype.

The amino acid sequence predicted from the DLF2 nucleic acid sequence was determined using GENSCAN and is presented in SEQ ID NO:2. A Basic BLASTP 2.0.11 search using the ncbi.nlm.nih.gov/BLAST website, was conducted. The BLASTP search using the predicted amino acid sequence of DLF2 revealed that DLF2 encodes a putative protein with homology to AP-2 transcription factors.

These results suggest that DLF2 is a newly discovered genes controlling plant height and flowering time in Arabidopsis.

EXAMPLE 3

Confirmation of Phenotype/Genotype Association

The dominant inheritance pattern of the DLF2 phenotype was confirmed through genetic analysis. In general, genetic analysis involves the production and analysis of F1 hybrids. Typically, F1 crosses are carried out by collecting pollen from T$_2$ plants, which is used to pollinate wild type plants. Such crosses are carried out by taking approximately 4 flowers from each selected individual plants, and using the T$_2$ flower as the male pollen donor and flowers of the wild type plants as the female. 4–5 crosses are done for an individual of interest. Seed formed from crosses of the same individual are pooled, planted and grown to maturity as F1 hybrids.

A number of F$_1$ hybrids from homozygous DLF2 parents showed the compact stature, late flowering, and increased chlorophyll phenotype, as shown in Table 1, above. F$_1$ flowers slightly earlier than homozygous T$_4$ plants, suggesting that the DLF2 mutation is dominant or semi-dominant.

EXAMPLE 4

Confirmation of Phenotype/Genotype Association in Arabidopsis

In order to further confirm the association between the DLF2 phenotype and the DLF2 gene presented in SEQ ID NO: 1, a genomic fragment comprising the DLF2 gene, provided in SEQ ID NO:3, was over-expressed in wild type Arabidopsis plants. The full-length DLF2 coding region was recovered from Line W000010438 plants by plasmid rescue. A fragment that included the 711 bp DLF2 fragment was cloned into the binary vector pAG2370. pAG2370, whose sequence is provided in SEQ ID NO:4, comprises the vector backbone from the vector pBIN19 (GI1256363), T-DNA left and right border fragments, and, between border fragments, the CsVMV promoter sequence and a Nos termination sequence for controlling expression of the inserted gene, and the neomycin phosphotransferase (NPTII) gene, which confers kanamycin resistance, whose expression is controlled by the RE4 promoter (U.S. Pat. No. 6,054,635) and the G7 termination sequence. The DLF2 fragment was inserted between the CsVMV promoter region, proximal to the 5' end of genomic fragment, and the Nos termination sequence, proximal to the 3' end of the genomic fragment. The pAG2370-DLF2 construct was transformed into Agrobacterium tumefaciens by electroporation.

Wild type Arabidopsis (COL-0) plants were transformed with pAG2370-DLF2 using standard vacuum infiltration methods. All infiltrated seeds were plated in selective media (approximately 60 µg/ml kanamycin), and kanamycin-resistant T$_1$ plants were transplanted to 72-cell flats. The transformation process generated 36 independent T$_0$ events. Morphological observations demonstrated that nine events had the same phenotype, showing late flowering and compact stature, as the original ACTTAG mutant DLF2. Tissue was collected from six T$_1$ plants showing different degrees of the DLF2 phenotype—five plants showed a strong DLF2 phenotype, and one showed a weak phenotype—and RT-PCR was carried out using wild type as control. The five T$_1$ lines with strong phenotype showed a very high level accumulation of DLF2 transcripts, whereas the weak phenotype individual had much less and wild type showed no detectable DLF2-1 transcripts. The internal control experiments, using a constitutively expressed protein kinase gene, showed that all samples had the same level of the kinase expression.

EXAMPLE 5

Confirmation of Phenotype/Genotype Association in Tomato

In order to further confirm the association between the DLF2 phenotype and the DLF2 gene in plants other than Arabidopsis, particularly in fruit-bearing plants, the DLF2 gene was introduced into and over-expressed in wild type *Lycopersicum esculentum* (tomato) plants.

The pAG2370-DLF2 construct described above was introduced into wild-type tomato plants via Agrobacterium-mediated transformation, essentially as described in PCT application WO0053794. Briefly, explants were dissected from tomato seedlings. Explants were inoculated by soaking in the Agrobacterium suspension for 15 to 120 minutes, blotted on sterile filter paper to remove excess bacteria, and plated. Explants were co-cultivated in non-selective media for 2–4 days at 24° C. with a 16-hour photoperiod, after which they were transferred to selective media (with kanamycin) and returned to the growth room. Explants were transferred to fresh medium every two weeks until shoots were 0.5 to 1 cm tall. Shoots were excised from the explants, placed on selective medium with kanamycin in Phytatrays (Sigma), and returned to the growth room for two to four weeks. Shoots were observed for rooting, and rooted shoots were out-planted to soil and acclimated to the greenhouse. The transformation process generated 27 independent $T_0$ events, of which three displayed the DLF2 mutant phenotype of compact stature, late flowering, and increased chlorophyll.

EXAMPLE 6

Confirmation of Phenotype/Genotype Association in Tobacco

In order to further confirm the association between the DLF2 phenotype and the DLF2 gene in plants other than Arabidopsis, the DLF2 gene was introduced into and over-expressed in wild type in Nicotiana tabacum (tobacco, Wisconsin-38 type).

The pAG2370-DLF2 construct described above was introduced into wild-type tobacco plants via Agrobacterium-mediated transformation. In order to generate tobacco plants for transformation, tobacco seeds were germinated as follows: seeds were shaken about ten minutes on a lab shaker, in a solution containing approximately 1.3% to 2.1% sodium hypochlorite and one drop of Tween-20 (Polyoxyethylenesorbitan monolaurate) per 100 milliliters. Seeds were then washed in sterile water and sterilely transferred to the surface of TbSG medium (4.3 g/l Murashige and Skoog salts, Phytotech; 1 ml/l MS vitamins, Sigma; 30 g/l sucrose; 8 g/l agar, Sigma; pH adjusted to ~5.8) in petri dishes or Phytatrays (Sigma), 10–50 seeds per vessel, and incubated in light at 25° C. Tobacco plants were dissected on sterile filter paper moistened with sterile, deionized water or liquid TbCo medium (4.3 g/l Murashige and Skoog salts, Phytotech; 1 ml/l MS vitamins, Sigma; 30 g/l sucrose; 200 mg/l $KH_2PO_4$; 2 mg/l Indole-3-acetic acid; 0.25 mg/l Kinetin; 0 to 100 $\mu$M Acetosyringone; 7 g/l Agar, Sigma; pH adjusted to 5.4–5.6). Explants with cut edges on all sides could be generated by cutting the leaf from the plant, dissecting out and discarding the midvein, and cutting the leaf lamina into 3 to 5 mm squares. Alternatively, discs could be cut from the lamina using a sterilized cork borer.

Explants were inoculated by soaking for 15–120 minutes in Agrobacterium suspension ($OD_{600}$ between 0.175 and 0.225) prepared with the pAG2370-DLF2 construct, then blotted and plated on TbCo medium. Explants were co-cultivated 2–4 days at 24° C. with a 16-hour photoperiod, and then transferred to Tb selective medium (4.3 g/l Murashige and Skoog salts; 1 ml/l Nitsch and Nitsch vitamins, Duchefa; 30 g/l sucrose; 0.5 to 2 mg/l 6-Benzylaminopurine; 0 to 1 mg/l Naphthylacetic Acid; 0 to 750 mg/l Carbenicillin; 0 to 300 mg/l Timentin; 0 to 500 mg/l Kanamycin; 7 to 8 g/l Agar, Sigma; pH adjusted to ~5.8) containing kanamycin and re-transferred every two weeks until shoots were 0.5 to 1 cm tall. Shoots were excised from the explants, placed on TbR medium (4.3 g/l Murashige and Skoog salts; 1 ml/l Nitsch and Nitsch vitamins, Duchefa; 30 g/l sucrose; 0 to 1 mg/l Indole-3-butyric acid; 0 to 1 mg/l Naphthylacetic Acid; 0 to 100 mg/l Carbenicillin; 0 to 200 mg/l Timentin; 0 to 100 mg/l Kanamycin; 7 to 8 g/l Agar, Sigma; pH adjusted to ~5.8.) with kanamycin in Phytatrays, and grown two to four weeks, after which time the rooted shoots were planted to soil.

The transformation process generated 24 independent $T_0$ events, of which two displayed the DLF2 mutant phenotype of compact stature, late flowering (observed as late seed maturation, even though the mutant plant flowered at the same time as the control), and increased chlorophyll.

REFERENCES

Altschul, S. F. et al., *J. Mol. Biol.* 215:403–410, 1990.

Altschul, S. F. et al., *Nucleic Acids Res.* 25:3389–3402, 1997.

Ausubel F M et al. Current Protocols in Molecular Biology, John Wiley & Sons, New York, N.Y., 1993.

Baldwin D et al., *Cur Opin Plant Biol.* 2(2):96–103, 1999.

Baulcombe D, *Arch Virol Suppl* 15:189–201, 1999.

Behringer and Medford, *Plant Mol. Biol. Rep.* 10(2) :190–198, 1992.

Carter et al., *Nucl. Acids Res.* 13:4331, 1986.

Choe A et al., Plant Cell, 10: 231–43, 1998.

Christensen S et al., 9th International Conference on Arabidopsis Research. Univ. of Wisconsin-Madison, Jun. 24–28, 1998. Abstract 165.

Cough, S J and Bent, A F, the *Plant Journal* 16(6): 735–743, 1998.

Crameri A and Stemmer W P, *Bio Techniques* 18(2) :194–6, 1995.

Creighton, T. E., PROTEINS: STRUCTURE AND MOLECULAR PROPERTIES, W. H. Freeman & Co., San Francisco, pp. 79–86, 1983.

Doolittle, R. F., OF URFS and ORFS (University Science Books, CA, 1986.)

Fang G et al., *Plant Cell.*, 1(1): 141–50, 1989.

Feldman et al., *Science* 243: 1351–1354, 1989.

Fridborg I et al., *Plant Cell* 11: 1019–1032, 1999.

Geest A H and Hall T C, *Plant Mol Biol* 32(4):579–88, 1996).

Gelvin, S. B., Schilperoort, R. A., Varma, D. P. S., eds. Plant Molecular Biology Manual 1990.

Glick, B R and Thompson, J E, Eds. METHODS IN PLANT MOLECULAR BIOLOGY AND BIOTECHNOLOGY, p. 213–221, CRC Press, 1993.

Harling et al., *EMBO J.* 16: 5855–66, 1997.

Haught C et al. *BioTechniques* 16(1):47–48, 1994.

Hayashi H et al., *Science* 258: 1350–1353, 1992.

Jacobsen S E et al., Proc Natl Acad Sci USA, 93:9292–6, 1996.

Jakobovits, A, et al., Ann N Y Acad Sci 764:525–35, 1995.

Jakobovits, A, Curr Opin Biotechnol 6(5):561–6, 1995.

Jensen, L. G., et al., *Proc. Natl. Acad. Sci. USA* 93:3487–3491, 1996.

Jones et al., *Nature* 321:522–525, 1986.
Jones J D et al, Transgenic Res 1:285–297 1992.
Kakimoto, *Science* 274: 982–5, 1996.
Kardailsky I et al., *Science* 286: 1962–1965, 1999.
Kohler and Milstein, *Nature* 256:495, 1975.
Kunkel T A et al., *Methods Enzymol.* 204:125–39, 1991.
Li J, Chory J, Cell, 90: 929–38, 1997.
Liu et al. *Plant Journal* 8(3) 457–463, 1995.
Marks and Feldman, *Plant Cell* 1:1053–1050, 1989.
Michaels S D, Amasina R M. Dev Genet. 25:194–8, 1999.
Miklashevichs et al. *Plant J*. 12: 489–98, 1997.
Napp-Zinn K, 1985. Arabidopsis thaliana. In HA Halevy, ed, Handbook of Flowering, Vol 1. CRC Press, Boca Raton, Fla., pp 492–503.
Napoli, et al, *Plant Cell* 2:279–289, 1990.
Novak, J and Novak, L, Promega Notes Magazine Number 61:27, 1997.
Omirulleh et al., Plant Mol Biol. 21(3):415–28, 1993.
Peng J et al., Genes Dev., 11:3194–205 1997.
Riechmann et al., *Nature* 332:323–327, 1988.

Sambrook et al. Molecular Cloning: A Laboratory Manual (Second Edition), Cold Spring Harbor Press, Plainview, N.Y.,1989.
Schaffer R, et al., *Cell* 93: 1219–1229, 1998.
Schell et al., Trends Plant Sci. 3: 130, 1998.
Smith, et al., *Nature* 334:724–726, 1988.
Van Haaren M J J et al., Plant Mol Bio 21:625–640, 1993.
Verdaguer B et al., Plant Mol Biol 37:1055–1067, 1998.
Verhoeyen et al., *Science* 239:1534–1536, 1988.
Walden et. al., *EMBO J*. 13: 4729–36, 1994.
Walden et al., *Plant Mol. Biol.* 26: 1521–8, 1994.
Waterhouse, et al., *Proc. Natl. Acad. Sci. USA* 95:13959–13964, 1998.
Wells et al., *Gene* 34:315, 1985.
Wells et al., *Philos. Trans. R. Soc.* London SerA 317:415, 1986.
Weigel D, et al., *Plant Physiology*, 122:1003–1013, 2000.
Wilson K et al., *Plant Cell* 8: 659–671, 1996.
Xu YL, et al., *Plant Cell*, 11: 927–36, 1999.
Zoller et al., *Nucl. Acids Res.* 10:6487, 1987.

It is claimed:

1. An isolated polynucleotide comprising a nucleic acid sequence that encodes or is complementary to a sequence that encodes a DLF2 polypeptide, wherein the DLF2 polypeptide has the amino acid sequence presented as SEQ ID NO:2.

2. The polynucleotide of claim 1 comprising the nucleic acid sequence presented as SEQ ID NO:1, or the complement thereof.

3. A plant transformation vector comprising the isolated polynucleotide of claim 1.

4. A transgenic plant cell transformed with the vector of claim 3.

5. A method of producing a late flowering and compact stature phenotype in a plant, said method comprising introducing into cells of the plant a plant transformation vector according to claim 3 and growing the transformed cells to produce a transgenic plant, wherein said polynucleotide sequence is expressed and said transgenic plant exhibits a late flowering and compact stature phenotype.

6. A plant part obtain by a method of claim 5.

* * * * *

SEQUENCE LISTING

<160> NUMBER OF SEQ ID NOS: 4

<210> SEQ ID NO 1
<211> LENGTH: 600
<212> TYPE: DNA
<213> ORGANISM: Arabidopsis thaliana

<400> SEQUENCE: 1

```
atgaggccta agaagcgtgc gggaaggaga gtgtttaagg agacacgtca cccagtttac      60
agaggcataa ggcggaggaa cggtgacaaa tgggtctgcg aagtcagaga accgacgcac     120
caacgccgca tttggctcgg gacttatccc acagcagata tggcagcgcg tgcacacgac     180
gtggcggttt tagctctgcg tgggagatcc gcatgtttga atttcgccga ctccgcttgg     240
cggcttccgg tgccggaatc caatgatccg gatgtgataa gaagagttgc ggcggaagct     300
gcggagatgt ttaggccggt ggatttagaa agtggaatta cggttttgcc ttgtgcggga     360
gatgatgtgg atttgggttt tggttcgggt tccggctctg gttcgggatc ggaggagagg     420
aattcttctt cgtatggatt tggagactac gaagaagtct caacgacgat gatgagactc     480
gcggaggggc cactaatgtc gccgccgcga tcgtatatgg aagacatgac tcctactaat     540
gtttacacgg aagaagagat gtgttatgaa gatatgtcat tgtggagtta cagatattaa     600
```

<210> SEQ ID NO 2
<211> LENGTH: 199
<212> TYPE: PRT
<213> ORGANISM: Arabidopsis thaliana

<400> SEQUENCE: 2

```
Met Arg Pro Lys Lys Arg Ala Gly Arg Arg Val Phe Lys Glu Thr Arg
 1               5                  10                  15

His Pro Val Tyr Arg Gly Ile Arg Arg Arg Asn Gly Asp Lys Trp Val
             20                  25                  30

Cys Glu Val Arg Glu Pro Thr His Gln Arg Arg Ile Trp Leu Gly Thr
         35                  40                  45
```

```
Tyr Pro Thr Ala Asp Met Ala Ala Arg Ala His Asp Val Ala Val Leu
     50                  55                  60

Ala Leu Arg Gly Arg Ser Ala Cys Leu Asn Phe Ala Asp Ser Ala Trp
 65                  70                  75                  80

Arg Leu Pro Val Pro Glu Ser Asn Asp Pro Asp Val Ile Arg Arg Val
                 85                  90                  95

Ala Ala Glu Ala Ala Glu Met Phe Arg Pro Val Asp Leu Glu Ser Gly
                100                 105                 110

Ile Thr Val Leu Pro Cys Ala Gly Asp Asp Val Asp Leu Gly Phe Gly
                115                 120                 125

Ser Gly Ser Gly Ser Gly Ser Glu Glu Arg Asn Ser Ser Ser
    130                 135                 140

Tyr Gly Phe Gly Asp Tyr Glu Glu Val Ser Thr Thr Met Met Arg Leu
145                 150                 155                 160

Ala Glu Gly Pro Leu Met Ser Pro Pro Arg Ser Tyr Met Glu Asp Met
                165                 170                 175

Thr Pro Thr Asn Val Tyr Thr Glu Glu Glu Met Cys Tyr Glu Asp Met
                180                 185                 190

Ser Leu Trp Ser Tyr Arg Tyr
            195

<210> SEQ ID NO 3
<211> LENGTH: 711
<212> TYPE: DNA
<213> ORGANISM: Arabidopsis thaliana

<400> SEQUENCE: 3
cccgggggac ggagatgagg cctaagaagc gtgcgggaag gagagtgttt aaggagacac      60
gtcacccagt ttacagaggc ataaggcgga ggaacggtga caaatgggtc tgcgaagtca     120
gagaaccgac gcaccaacgc cgcatttggc tcgggactta tcccacagca gatatggcag     180
cgcgtgcaca cgacgtggcg gttttagctc tgcgtgggag atccgcatgt ttgaatttcg     240
ccgactccgc ttggcggctt ccggtgccgg aatccaatga tccggatgtg ataagaagag     300
ttgcggcgga agctgcggag atgtttaggc cggtggattt agaaagtgga attacggttt     360
tgccttgtgc gggagatgat gtggatttgg gttttggttc gggttccggc tctggttcgg     420
gatcggagga gaggaattct tcttcgtatg gatttggaga ctacgaagaa gtctcaacga     480
cgatgatgag actcgcggag gggccactaa tgtcgccgcc gcgatcgtat atggaagaca     540
tgactcctac taatgtttac acggaagaag agatgtgtta tgaagatatg tcattgtgga     600
gttacagata ttaagtggga ctcacatatc tactatacat aatatttagc ttttatgtaa     660
gaggtattta tgtgagtttt aagattgtag atgtgtccca ggccgtctag a              711

<210> SEQ ID NO 4
<211> LENGTH: 12241
<212> TYPE: DNA
<213> ORGANISM: vector, multiple sequences

<400> SEQUENCE: 4
tgagcgtcgc aaaggcgctc ggtcttgcct tgctcgtcgg tgatgtactt caccagctcc      60
gcgaagtcgc tcttcttgat ggagcgcatg gggacgtgct tggcaatcac gcgcaccccc     120
cggccgtttt agcggctaaa aaagtcatgg ctctgccctc gggcggacca cgcccatcat     180
gaccttgcca agctcgtcct gcttctcttc gatcttcgcc agcagggcga ggatcgtggc     240
atcaccgaac cgcgccgtgc gcgggtcgtc ggtgagccag agtttcagca ggccgcccag     300
```

-continued

```
gcggcccagg tcgccattga tgcgggccag ctcgcggacg tgctcatagt ccacgacgcc    360
cgtgattttg tagccctggc cgacggccag caggtaggcc gacaggctca tgccggccgc    420
cgccgccttt tcctcaatcg ctcttcgttc gtctggaagg cagtacacct tgataggtgg    480
gctgcccttc ctggttggct tggtttcatc agccatccgc ttgccctcat ctgttacgcc    540
ggcggtagcc ggccagcctc gcagagcagg attcccgttg agcaccgcca ggtgcgaata    600
agggacagtg aagaaggaac acccgctcgc gggtgggcct acttcaccta tcctgcccgg    660
ctgacgccgt tggatacacc aaggaaagtc tacacgaacc ctttggcaaa atcctgtata    720
tcgtgcgaaa aaggatggat ataccgaaaa aatcgctata atgaccccga agcagggtta    780
tgcagcggaa aagcgccacg cttcccgaag ggagaaaggc ggacaggtat ccggtaagcg    840
gcagggtcgg aacaggagag cgcacgaggg agcttccagg gggaaacgcc tggtatcttt    900
atagtcctgt cgggtttcgc cacctctgac ttgagcgtcg attttttgtga tgctcgtcag    960 gggggcggag cctatggaaa aacgccagca acgcggcctt tttacggttc ctggccttt     1020 gctggccttt tgctcacatg ttctttcctg cgttatcccc tgattctgtg gataaccgta    1080
ttaccgcctt tgagtgagct gataccgctc gccgcagccg aacgaccgag cgcagcgagt    1140
cagtgagcga ggaagcggaa gagcgccaga aggccgccag agaggccgag cgcggccgtg    1200
aggcttggac gctagggcag ggcatgaaaa agcccgtagc gggctgctac gggcgtctga    1260
cgcggtggaa aggggggagg gatgttgtct acatggctct gctgtagtga gtgggttgcg    1320
ctccggcagc ggtcctgatc aatcgtcacc ctttctcggt ccttcaacgt tcctgacaac    1380
gagcctcctt tcgccaatc  catcgacaat caccgcgagt ccctgctcga acgctgcgtc    1440
cggaccggct tcgtcgaagg cgtctatcgc ggcccgcaac agcggcgaga cggagcctg    1500 ttcaacggtg ccgccgcgct cgccggcatc gctgtcgccg gctgctcct caagcacggc    1560 cccaacagtg aagtagctga ttgtcatcag cgcattgacg gcgtccccgg ccgaaaaacc    1620
cgcctcgcag aggaagcgaa gctgcgcgtc ggccgtttcc atctgcggtg cgcccggtcg    1680
cgtgccggca tggatgcgcg cgccatcgcg gtaggcgagc agcgcctgcc tgaagctgcg    1740
ggcattcccg atcagaaatg agcgccagtc gtcgtcggct ctcggcaccg aatgcgtatg    1800
attctccgcc agcatggctt cggccagtgc gtcgagcagc gcccgcttgt tcctgaagtg    1860
ccagtaaagc gccggctgct gaaccccccaa ccgttccgcc agtttgcgtg tcgtcagacc    1920
gtctacgccg acctcgttca acaggtccag ggcggcacgg atcactgtat tcggctgcaa    1980 cttttgtcatg cttgacactt tatcactgat aaacataata tgtccaccaa cttatcagtg    2040
ataaagaatc cgcgcgttca atcggaccag cggaggctgg tccggaggcc agacgtgaaa    2100
cccaacatac ccctgatcgt aattctgagc actgtcgcgc tcgacgctgt cggcatcggc    2160
ctgattatgc cggtgctgcc gggcctcctg cgcgatctgt tcactcgaa cgacgtcacc    2220 gcccactatg gcattctgct ggcgctgtat gcgttggtgc aatttgcctg cgcacctgtg    2280
ctgggcgcgc tgtcggatcg tttcgggcgg cggccaatct tgctcgtctc gctggccggc    2340
gccagatctg ggaaccctg tggttggcat gcacatacaa atggacgaac ggataaacct    2400
tttcacgccc ttttaaatat ccgattattc taataaacgc tcttttctct taggtttacc    2460
cgccaatata tcctgtcaaa cactgatagt ttaaactgaa ggcgggaaac gacaatctga    2520
tcatgagcgg agaattaagg gagtcacgtt atgacccccg ccgatgacgc gggacaagcc    2580
gttttacgtt tggaactgac agaaccgcaa cgttgaagga gccactcagc cgatctgaat    2640
```

-continued

| | | | | |
|---|---|---|---|---|
| tcccgatcta | gtaacataga | tgacaccgcg | cgcgataatt | tatcctagtt tgcgcgctat | 2700 |
| attttgtttt | ctatcgcgta | ttaaatgtat | aattgcggga | ctctaatcat aaaaacccat | 2760 |
| ctcataaata | acgtcatgca | ttacatgtta | attattacat | gcttaacgta attcaacaga | 2820 |
| aattatatga | taatcatcgc | aagaccggca | acaggattca | atcttaagaa actttattgc | 2880 |
| caaatgtttg | aacgatcggg | gaaattcgcg | agctcggtac | ccgctctaga actagtggat | 2940 |
| cccccgggct | gcaggaattc | aaacttacaa | atttctctga | acttgtatcc tcagtacttc | 3000 |
| aaagaaaata | gcttacacca | aatttttcct | tgttttcaca | aatgccgaac ttggttcctt | 3060 |
| atataggaaa | actcaagggc | aaaaatgaca | cggaaaaata | taaaaggata agtagtgggg | 3120 |
| gataagattc | ctttgtgata | aggttacttt | ccgcccttac | attttccacc ttacatgtgt | 3180 |
| cctctatgtc | tctttcacaa | tcaccgacct | tatcttcttc | ttttcattgt tgtcgtcagt | 3240 |
| gcttacgtct | tcaagattct | tttcttcgcc | tggttcttct | ttttcaattt ctacgtattc | 3300 |
| ttcttcgtat | tctggcagta | taggatcttg | tatctgtaca | ttcttcattt ttgaacatag | 3360 |
| gttgcatatg | tgccgcatat | tgatctgctt | cttgctgagc | tcacataata cttccatagt | 3420 |
| ttttcccgta | aacattggat | tcttgatgct | acatcttgga | taattacctt ctcgtaccaa | 3480 |
| gcttaattga | gatgattagc | ccagacccag | caggattagg | cttaatggtg gtccatttga | 3540 |
| gaaaaagatt | aaaaatgatg | tcataaaaaa | acgtggtcgg | caggattcga acctgcgcgg | 3600 |
| gcaaagccca | catgatttct | agtcatgccc | gataaccact | ccggcacgac cacaatgatg | 3660 |
| ctacaattgc | tttgttgtaa | tcattaactt | atggttgagt | tgatgctga ttaatactat | 3720 |
| tatgtttcca | ttaactactt | ttgaagtata | caaaattacg | aatttataac caaatttgag | 3780 |
| gtataatatg | cgagagctac | ctaaattttt | cttacttaat | tttaaagtac attcaaattc | 3840 |
| tgaatttata | ttgtgtatag | tcagaaaaca | atctacatat | ttaaacacat aaatttctca | 3900 |
| cgtttataat | caattttgtc | ggttcctgta | attttctaa | aataaaaagc aaccaaaatt | 3960 |
| gtgcatcaac | ttattacata | ccatgggaaa | tgcaaacttc | aaaacttatg gactcaaagg | 4020 |
| gtacatatct | aaactacata | ttgtcagatt | cttcactctt | atttcttgag ggcctcgagg | 4080 |
| cattaccaac | caaatccaaa | aattgctttc | gaatctcaat | aaaaaggata accccatgaa | 4140 |
| aaagacgtgg | acggcaggat | tcgaacctgc | gcgcagagcc | cacatgattt ctagtcatgc | 4200 |
| ccgataacca | ctccggcacg | tccacttcac | tgttaacgtt | tacagtaaca agtcactaac | 4260 |
| tactaatcaa | cattagctca | ggaaatcaaa | actagattat | ttacatttac aacgacatgt | 4320 |
| cgttcgaagt | agttggtctg | tatctgagta | gctttggcgg | gtagattcaa tcgcatttct | 4380 |
| gcatataaaa | ctgatcctcc | ctctatcgcc | aaagtcaaac | tgaaaagggc cgggggcaag | 4440 |
| atatgggagc | ttggattgaa | caagatggat | tgcacgcagg | ttctccggcc gcttgggtgg | 4500 |
| agaggctatt | cggctatgac | tgggcacaac | agacaatcgg | ctgctctgat gccgccgtgt | 4560 |
| tccggctgtc | agcgcagggg | cgcccggttc | ttttgtcaa | gaccgacctg tccggtgccc | 4620 |
| tgaatgaact | gcaggacgag | gcagcgcggc | tatcgtggct | ggccacgacg ggcgttcctt | 4680 |
| gcgcagctgt | gctcgacgtt | gtcactgaag | cgggaaggga | ctggctgcta ttgggcgaag | 4740 |
| tgccggggca | ggatctcctg | tcatctcacc | ttgctcctgc | cgagaaagta tccatcatgg | 4800 |
| ctgatgcaat | gcggcggctg | catacgcttg | atccggctac | ctgcccattc gaccaccaag | 4860 |
| cgaaacatcg | catcgagcga | gcacgtactc | ggatggaagc | cggtcttgtc gatcaggatg | 4920 |
| atctggacga | agagcatcag | gggctcgcgc | cagccgaact | gttcgccagg ctcaaggcgc | 4980 |
| gcatgcccga | cggcgaggat | ctcgtcgtga | cccatggcga | tgcctgcttg ccgaatatca | 5040 |

```
tggtggaaaa tggccgcttt tctggattca tcgactgtgg ccggctgggt gtggcggacc    5100
gctatcagga catagcgttg gctacccgtg atattgctga agagcttggc ggcgaatggg    5160
ctgaccgctt cctcgtgctt tacggtatcg ccgctcccga ttcgcagcgc atcgccttct    5220
atcgccttct tgacgagttc ttctgacgat gagctaagct agctatatca tcaatttatg    5280
tattacacat aatatcgcac tcagtctttc atctacggca atgtaccagc tgatataatc    5340
agttattgaa atatttctga atttaaactt gcatcaataa atttatgttt ttgcttggac    5400
tataatacct gacttgttat tttatcaata aatatttaaa ctatatttct ttcaagatgg    5460
gaattaattc actggccgtc gttttacaac gtcgtgactg ggaaaaccct ggcgttaccc    5520
aacttaatcg ccttgcagca catccccctt tcgccagctg gcgtaatagc gaagaggccc    5580
gcaccgatcg cccttcccaa cagttgcgca gcctgaatgg cgcccgctcc tttcgctttc    5640
ttcccttcct ttctcgccac gttcgccggc tttccccgtc aagctctaaa tcgggggctc    5700
cctttagggt tccgatttag tgctttacgg cacctcgacc ccaaaaaact tgatttgggt    5760
gatggttcac gtagtgggcc atcgccctga tagacggttt ttcgcccttt gacgttggag    5820
tccacgttct ttaatagtgg actcttgttc caaactggaa caacactcaa ccctatctcg    5880
ggctattctt ttgatttata agggattttg ccgatttcgg aaccaccatc aaacaggatt    5940
ttcgcctgct ggggcaaacc agcgtggacc gcttgctgca actctctcag gccaggcgg    6000 tgaagggcaa tcagctgttg cccgtctcac tggtgaaaag aaaaaccacc ccagtacatt    6060
aaaaacgtcc gcaatgtgtt attaagttgt ctaagcgtca atttgtttac accacaatat    6120
atcctgccac cagccagcca acagctcccc gaccggcagc tcggcacaaa atcaccactc    6180
gatacaggca gcccatcagt ccgggacggc gtcagcggga gagccgttgt aaggcggcag    6240
actttgctca tgttaccgat gctattcgga agaacggcaa ctaagctgcc gggtttgaaa    6300
cacggatgat ctcgcggagg gtagcatgtt gattgtaacg atgacagagc gttgctgcct    6360
gtgatcaaat atcatctccc tcgcagagat ccgaattatc agccttctta ttcatttctc    6420
gcttaaccgt gacaggctgt cgatcttgag aactatgccg acataatagg aaatcgctgg    6480
ataaagccgc tgaggaagct gagtggcgct atttctttag aagtgaacgt tgacgatatc    6540 aactcccta tccattgctc accgaatggt acaggtcggg gacccgaagt tccgactgtc    6600
ggcctgatgc atccccggct gatcgacccc agatctgggg ctgagaaagc ccagtaagga    6660
aacaactgta ggttcgagtc gcgagatccc ccggaaccaa aggaagtagg ttaaacccgc    6720
tccgatcagg ccgagccacg ccaggccgag aacattggtt cctgtaggca tcgggattgg    6780
cggatcaaac actaaagcta ctggaacgag cagaagtcct ccggccgcca gttgccaggc    6840
ggtaaaggtg agcagaggca cgggaggttg ccacttgcgg gtcagcacgg ttccgaacgc    6900
catggaaacc gccccgcca ggcccgctgc gacgccgaca ggatctagcg ctgcgtttgg    6960
tgtcaacacc aacagcgcca cgcccgcagt tccgcaaata gccccagga ccgccatcaa    7020 tcgtatcggg ctacctagca gagcggcaga gatgaacacg accatcagcg gctgcacagc    7080
gcctaccgtc gccgcgaccc cgcccggcag gcggtagacc gaaataaaca acaagctcca    7140
gaatagcgaa atattaagtg cgccgaggat gaagatcgc atccaccaga ttcccgttgg    7200
aatctgtcgg acgatcatca cgagcaataa acccgccggc aacgccgca gcagcatacc    7260 ggcgacccct cggcctcgct gttcgggctc acgaaaacg ccggacagat gcgccttgtg    7320
agcgtccttg gggccgtcct cctgtttgaa gaccgacagc ccaatgatct cgccgtcgat    7380
```

-continued

```
gtaggcgccg aatgccacgg catctcgcaa ccgttcagcg aacgcctcca tgggcttttt    7440
ctcctcgtgc tcgtaaacgg acccgaacat ctctggagct ttcttcaggg ccgacaatcg    7500
gatctcgcgc aaatcctgca cgtcggccgc tccaagccgt cgaatctgag ccttaatcac    7560
aattgtcaat tttaatcctc tgtttatcgg cagttcgtag agcgcgccgt gcgtcccgag    7620
cgatactgag cgaagcaagt gcgtcgagca gtgcccgctt gttcctgaaa tgccagtaaa    7680
gcgctggctg ctgaaccccc agccggaact gaccccacaa ggccctagcg tttgcaatgc    7740
accaggtcat cattgaccca ggcgtgttcc accaggccgc tgcctcgcaa ctcttcgcag    7800
gcttcgccga cctgctcgcg ccacttcttc acgcgggtgg aatccgatcc gcacatgagg    7860
cggaaggttt ccagcttgag cgggtacggg tcccggtgcg agctgaaata gtcgaacatc    7920
cgtcgggccg tcggcgacag cttgcggtac ttctcccata tgaatttcgt gtagtggtcg    7980
ccagcaaaca gcacgacgat ttcctcgtcg atcaggacct ggcaacggga cgttttcttg    8040
ccacggtcca ggacgcggaa gcggtgcagc agcgacaccg attccaggtg cccaacgcgg    8100
tcggacgtga agcccatcgc cgtcgcctgt aggcgcgaca ggcattcctc ggccttcgtg    8160
taataccggc cattgatcga ccagcccagg tcctggcaaa gctcgtagaa cgtgaaggtg    8220
atcggctcgc cgatagggt gcgcttcgcg tactccaaca cctgctgcca caccagttcg     8280
tcatcgtcgg cccgcagctc gacgccgtg taggtgatct tcacgtcctt gttgacgtgg      8340
aaaatgacct tgttttgcag cgcctcgcgc gggattttct tgttgcgcgt ggtgaacagg    8400
gcagagcggg ccgtgtcgtt tggcatcgct cgcatcgtgt ccggccacgg cgcaatatcg    8460
aacaaggaaa gctgcatttc cttgatctgc tgcttcgtgt gtttcagcaa cgcggcctgc    8520
ttggcctcgc tgacctgttt tgccaggtcc tcgccggcgg ttttttcgctt cttggtcgtc    8580 atagttcctc gcgtgtcgat ggtcatcgac ttcgccaaac ctgccgcctc ctgttcgaga    8640
cgacgcgaac gctccacggc ggccgatggc gcgggcaggg caggggagc cagttgcacg      8700 ctgtcgcgct cgatcttggc cgtagcttgc tggaccatcg agccgacgga ctggaaggtt    8760
tcgcggggcg cacgcatgac ggtgcggctt gcgatggttt cggcatcctc ggcggaaaac    8820
cccgcgtcga tcagttcttg cctgtatgcc ttccggtcaa acgtccgatt cattcaccct    8880
ccttgcggga ttgccccgac tcacgccggg gcaatgtgcc cttattcctg atttgacccg    8940
cctggtgcct tggtgtccag ataatccacc ttatcggcaa tgaagtcggt cccgtagacc    9000
gtctggccgt ccttctcgta cttggtattc cgaatcttgc cctgcacgaa taccagcgac    9060
cccttgccca aatacttgcc gtgggcctcg gcctgagagc caaaacactt gatgcggaag    9120
aagtcggtgc gctcctgctt gtcgccggca tcgttgcgcc acatctaggt actaaaacaa    9180
ttcatccagt aaaatataat attttatttt ctcccaatca ggcttgatcc ccagtaagtc    9240
aaaaaatagc tcgacatact gttcttcccc gatatcctcc ctgatcgacc ggacgcagaa    9300
ggcaatgtca taccacttgt ccgccctgcc gcttctccca agatcaataa agccacttac    9360
tttgccatct ttcacaaaga tgttgctgtc tcccaggtcg ccgtgggaaa agacaagttc    9420
ctcttcgggc ttttccgtct ttaaaaaatc atacagctcg cgcggatctt taaatggagt    9480
gtcttcttcc cagttttcgc aatccacatc ggccagatcg ttattcagta agtaatccaa    9540
ttcggctaag cggctgtcta agctattcgt ataggggacaa tccgatatgt cgatggagtg    9600
aaagagcctg atgcactccg catacagctc gataatcttt tcaggctttt gttcatcttc    9660
atactcttcc gagcaaagga cgccatcggc ctcactcatg agcagattgc tccagccatc    9720
atgccgttca agtgcagga ccttttggaac aggcagcttt ccttccagcc atagcatcat    9780
```

```
gtcctttttcc cgttccacat cataggtggt ccctttatac cggctgtccg tcattttttaa   9840 atataggttt tcattttctc ccaccagctt atataccta gcaggagaca ttccttccgt   9900
atcttttacg cagcggtatt tttcgatcag ttttttcaat tccggtgata ttctcatttt   9960
agccatttat tatttccttc ctcttttcta cagtatttaa agatacccca agaagctaat  10020
tataacaaga cgaactccaa ttcactgttc cttgcattct aaaaccttaa ataccagaaa  10080
acagcttttt caaagttgtt ttcaaagttg gcgtataaca tagtatcgac ggagccgatt  10140
ttgaaaccac aattatgggt gatgctgcca acttactgat ttagtgtatg atggtgtttt  10200
tgaggtgctc cagtggcttc tgtgtctatc agctgtccct cctgttcagc tactgacggg  10260
gtggtgcgta acggcaaaag caccgccgga catcagcgct atctctgctc tcactgccgt  10320
aaaacatggc aactgcagtt cacttacacc gcttctcaac ccggtacgca ccagaaaatc  10380
attgatatgg ccatgaatgg cgttggatgc cgggcaacag cccgcattat gggcgttggc  10440
ctcaacacga ttttacgtca cttaaaaaac tcaggccgca gtcggtaacc tcgcgcatac  10500
agccgggcag tgacgtcatc gtctgcgcgg aaatggacga acagtggggc tatgtcgggg  10560
ctaaatcgcg ccagcgctgg ctgttttacg cgtatgacag tctccggaag acggttgttg  10620
cgcacgtatt cggtgaacgc actatggcga cgctggggcg tcttatgagc ctgctgtcac  10680
cctttgacgt ggtgatatgg atgacggatg ctggccgct gtatgaatcc cgcctgaagg  10740
gaaagctgca cgtaatcagc aagcgatata cgcagcgaat tgagcggcat aacctgaatc  10800
tgaggcagca cctggcacgg ctgggacgga agtcgctgtc gttctcaaaa tcggtggagc  10860
tgcatgacaa agtcatcggg cattatctga acataaaaca ctatcaataa gttggagtca  10920
ttacccaatt atgatagaat ttacaagcta taaggttatt gtcctgggtt tcaagcatta  10980
gtccatgcaa gttttatgc tttgcccatt ctatagatat attgataagc gcgctgccta  11040
tgccttgccc cctgaaatcc ttacatacgg cgatatcttc tatataaaag atatattatc  11100
ttatcagtat tgtcaatata ttcaaggcaa tctgcctcct catcctcttc atcctcttcg  11160
tcttggtagc ttttttaaata tggcgcttca tagagtaatt ctgtaaaggt ccaattctcg  11220
ttttcatacc tcggtataat cttacctatc acctcaaatg gttcgctggg tttatcgcac  11280
ccccgaacac gagcacggca cccgcgacca ctatgccaag aatgcccaag gtaaaaattg  11340
ccggccccgc catgaagtcc gtgaatgcc cgacggccga agtgaagggc aggccgccac  11400
ccaggccgcc gccctcactg cccggcacct ggtcgctgaa tgtcgatgcc agcacctgcg  11460
gcacgtcaat gcttccgggc gtcgcgctcg ggctgatcgc ccatcccgtt actgccccga  11520
tcccggcaat ggcaaggact gccagcgctg ccatttttgg ggtgaggccg ttcgcggccg  11580
aggggcgcag cccctggggg gatgggaggc ccgcgttagc gggccgggag ggttcgagaa  11640 ggggggggcac cccccttcgg cgtgcgcggt cacgcgcaca gggcgcagcc ctggttaaaa  11700
acaaggttta taaatattgg tttaaaagca ggttaaaaga caggttagcg gtggccgaaa  11760
aacgggcgga aaccccttgca aatgctggat tttctgcctg tggacagccc ctcaaatgtc  11820
aataggtgcg cccctcatct gtcagcactc tgcccctcaa gtgtcaagga tcgcgcccct  11880
catctgtcag tagtcgcgcc cctcaagtgt caataccgca gggcacttat ccccaggctt  11940
gtccacatca tctgtgggaa actcgcgtaa atcaggcgt tttcgccgat ttgcgaggct  12000
ggccagctcc acgtcgccgg ccgaaatcga gcctgcccct catctgtcaa cgccgcgccg  12060
ggtgagtcgg cccctcaagt gtcaacgtcc gcccctcatc tgtcagtgag gccaagtttt  12120
```

```
                                                       -continued
tccgcgaggt atccacaacg ccggcggccg cggtgtctcg cacacggctt cgacggcgtt    12180
tctggcgcgt ttgcagggcc atagacggcc gccagcccag cggcgagggc aaccagcccg    12240
g                                                                    12241
```